(12) United States Patent
Kasahara

(10) Patent No.: US 7,125,386 B2
(45) Date of Patent: Oct. 24, 2006

(54) METHOD AND APPARATUS FOR JUDGMENT OF PHYSICAL CONSTITUTION AND PHYSICAL STRENGTH FOR PERSON UNDER TEST

(75) Inventor: Yasuhiro Kasahara, Tokyo (JP)

(73) Assignee: Tanita Corporation, Tokyo (JP)

( * ) Notice: Subject to any disclaimer, the term of this patent is extended or adjusted under 35 U.S.C. 154(b) by 343 days.

(21) Appl. No.: 10/645,752

(22) Filed: Aug. 20, 2003

(65) Prior Publication Data

US 2004/0064071 A1    Apr. 1, 2004

(30) Foreign Application Priority Data

Aug. 27, 2002 (JP) .............................. 2002-247808

(51) Int. Cl.
*A61B 5/103* (2006.01)
*A61B 5/117* (2006.01)

(52) U.S. Cl. ..................................... 600/595; 600/547

(58) Field of Classification Search ................ 600/547, 600/300

See application file for complete search history.

(56) References Cited

U.S. PATENT DOCUMENTS 6,269,339 B1 * 7/2001 Silver ........................... 705/2
6,468,209 B1 * 10/2002 Heymsfield et al. ........ 600/300
2001/0053883 A1 * 12/2001 Yoshimura et al. .......... 600/587

FOREIGN PATENT DOCUMENTS

| EP | 1 132 046 A1 | 9/2001 |
| EP | 1132046 A1 * | 9/2001 |
| EP | 1 201 187 A1 | 5/2002 |
| EP | 1 222 895 A1 | 7/2002 |
| JP | 10192258 | 7/1998 |

OTHER PUBLICATIONS

Kyle, Ursula, et al. *Body Composition Interpretation: Contributions of the Fat-Free Mass Index and the Body Fat Mass Index*, Nutrition vol. 19 pp. 597-604, 2003, published Geneva University Hospital, Geneva, Switzerland.

* cited by examiner

*Primary Examiner*—Max F. Hindenburg
*Assistant Examiner*—Anuradha Roy
(74) *Attorney, Agent, or Firm*—Fulwider Patton LLP

(57) ABSTRACT

A method and an apparatus for judgment of physical constitution and physical strength for a person under test are described. The apparatus comprises a first input unit, a second input unit, and an arithmetic unit. According to the present invention the first input unit enters fat mass in a trunk of the person under test. The second input unit enters fat mass in lower limbs of the person under test. The arithmetic unit calculates Proportion Age based on the data entered from said first and second input units.

6 Claims, 20 Drawing Sheets

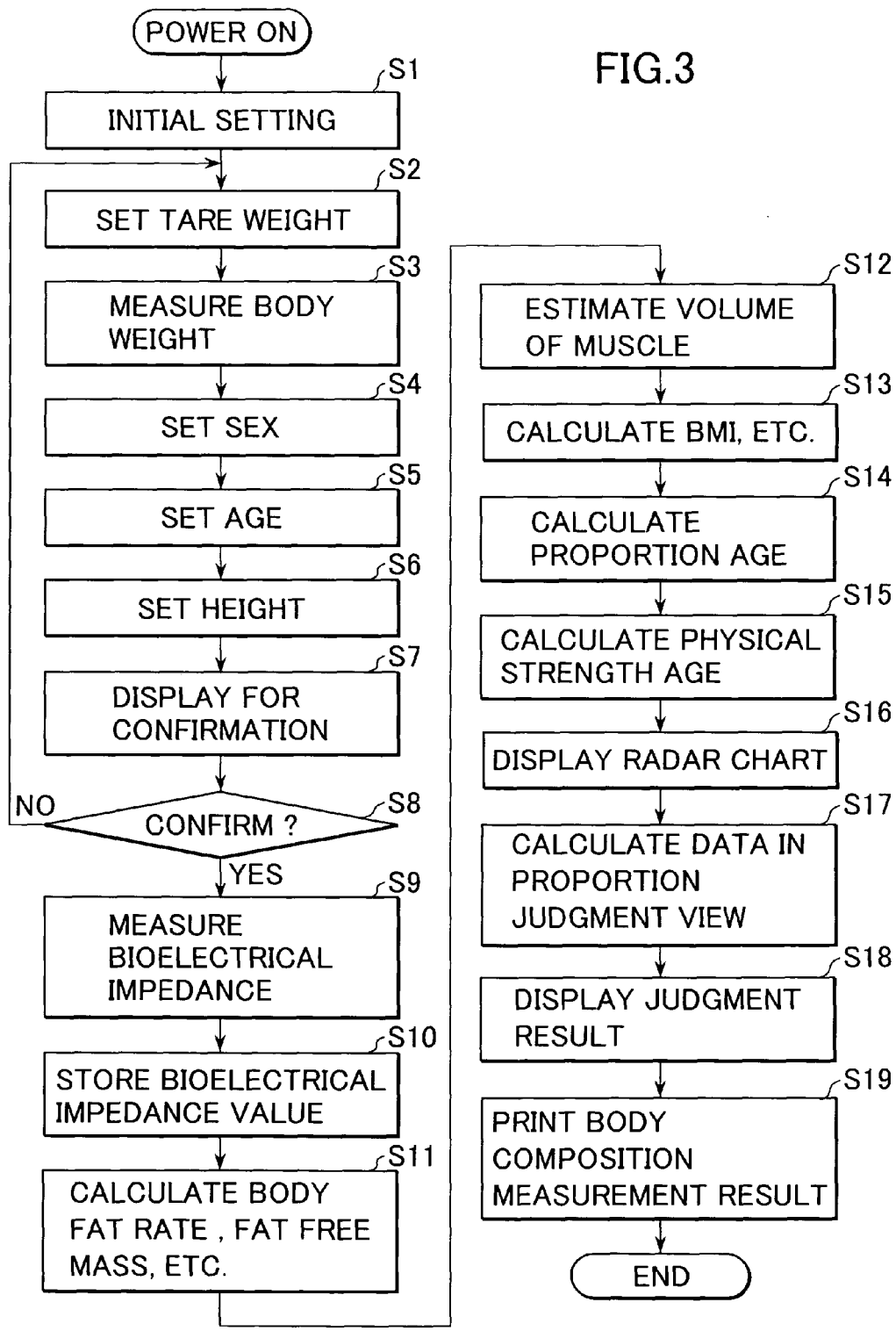

FIG.4A

```
ENTER TARE WEIGHT                    [RETURN]
                                     [PROCEED]
   TARE WEIGHT              Kg

[7]    [8]    [9]
     [4]    [5]    [6]
     [1]    [2]    [3]    [ERASE]
            [0]    [ ]    [BACK]
```

FIG.4B

```
ENTER TARE WEIGHT                    [RETURN]
                                     [PROCEED]
   TARE WEIGHT           1.5Kg

[7]    [8]    [9]
     [4]    [5]    [6]
     [1]    [2]    [3]    [ERASE]
            [0]    [ ]    [BACK]
```

FIG.4C

```
MEASURE BODY WEIGHT                  [RETURN]
MOUNT ON PLATFORM WITH BARE FEET     [PROCEED]

SUBTRACT TARE WEIGHT

RETURN
PROCEED

BODY WEIGHT:
　　SUBTRACT TARE WEIGHT 50.2Kg

PROCEED TO NEXT STEP AND ENTER NECESSARY ITEMS

FIG.4E

ENTER BODY BUILD AND SEX

RETURN
PROCEED

| STANDARD MAN | STANDARD WOMAN |
|---|---|
| ATHLETE MAN | ATHLETE WOMAN |

FIG.4F

ENTER AGE

RETURN
PROCEED

AGE　　　　　　　YEARS OLD

| 7 | 8 | 9 |  |
|---|---|---|---|
| 4 | 5 | 6 |  |
| 1 | 2 | 3 | ERASE |
|   | 0 | . | BACK |

FIG.5A

ENTER HEIGHT                                      RETURN
                                                  PROCEED
    HEIGHT              cm

[ 7 ]   [ 8 ]   [ 9 ]
    [ 4 ]   [ 5 ]   [ 6 ]
    [ 1 ]   [ 2 ]   [ 3 ]   [ ERASE ]
            [ 0 ]   [ . ]   [ BACK ]

FIG.5B

COMFIRM CONTENT THAT HAVE BEEN          RETURN
SET AND DEPRESS START KEY

[ START ]   [ STOP ]

CONTENT THAT HAVE BEEN SET
(DEPRESS RETURN KEY FOR CORRECTION)

| BODY WEIGHT: 50.2Kg | BODY BUILD:STANDARD/MAN |
| AGE: 73 | HEIGHT: 156cm |

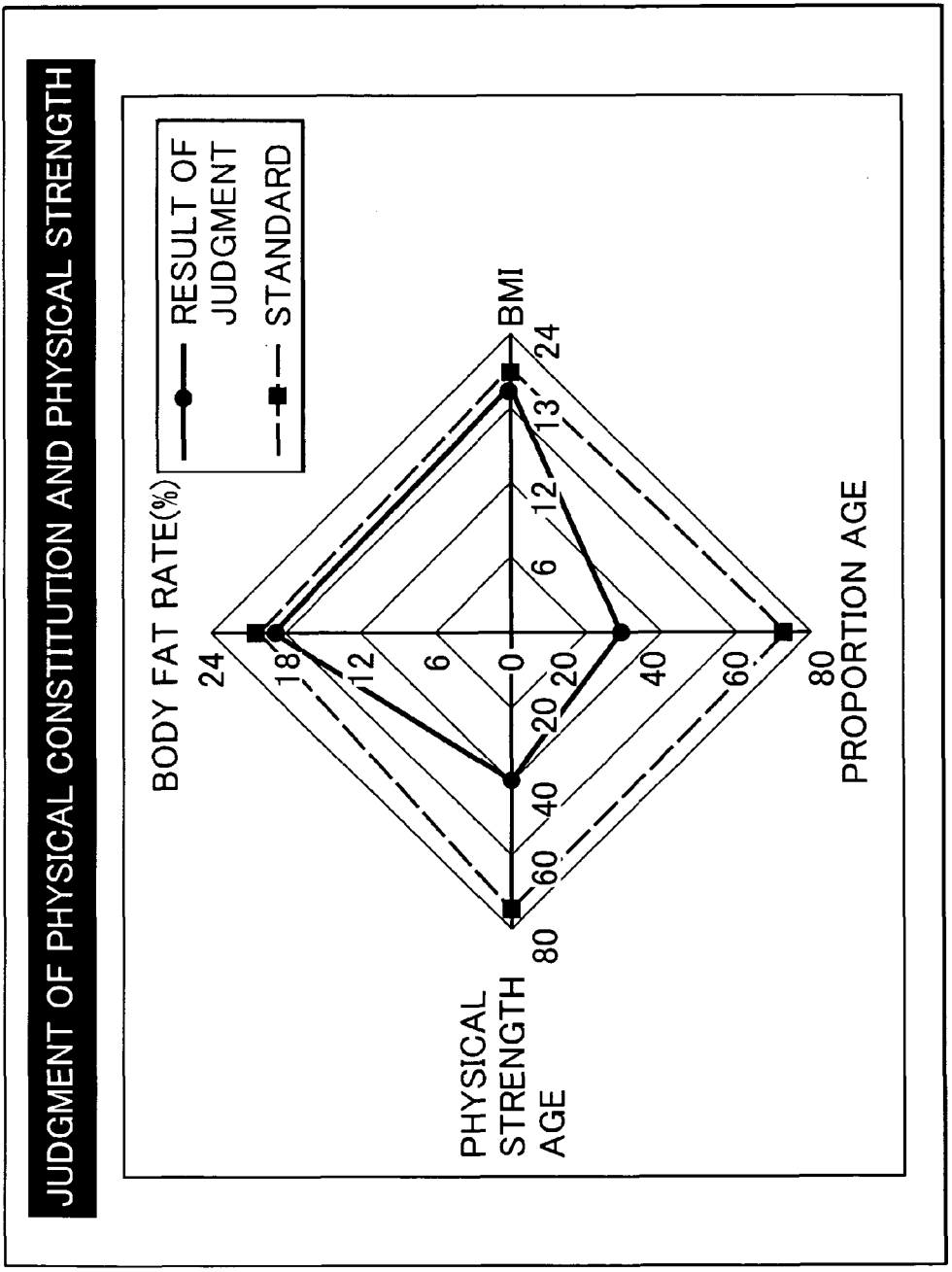

FIG.10

PROPORTION JUDGMENT VIEW

TRUNK

| FAT RATE | 20.4% |
| FAT MASS | 5.9Kg |
| FAT FREE MASS | 23Kg |
| ESTIMATED VOLUME OF MUSCLE | 21.8Kg |

LEFT ARM

| FAT RATE | 11.5% |
| FAT MASS | 0.3Kg |
| FAT FREE MASS | 2.3Kg |
| ESTIMATED VOLUME OF MUSCLE | 2.1Kg |

LEFT LEG

| FAT RATE | 17.7% |
| FAT MASS | 1.4Kg |
| FAT FREE MASS | 6.5Kg |
| ESTIMATED VOLUME OF MUSCLE | 6.1Kg |

RIGHT ARM

| FAT RATE | 14.3% |
| FAT MASS | 0.4Kg |
| FAT FREE MASS | 2.4Kg |
| ESTIMATED VOLUME OF MUSCLE | 2.3Kg |

RIGHT LEG

| FAT RATE | 17.3% |
| FAT MASS | 1.4Kg |
| FAT FREE MASS | 6.7Kg |
| ESTIMATED VOLUME OF MUSCLE | 6.2Kg |

FIG.11

| RESULT OF JUDGMENT |
|---|
| YOU HAVE PROPER VALUE FOR BMI, BUT TEND TOWARD ADIPOSITY IN WHICH BODY FAT IS GREATER. IN ADDITION, YOU HAVE HIGHER PHYSICAL STRENGTH AGE, AND HAVE RELATIVELY LOWER VOLUME OF LEG MUSCLE. |

FIG.14

| WHOLE BODY COMPOSITION DIAGNOSIS | | UPPER-HALF AND LOWER-HALF BODIES BALANCE | |
|---|---|---|---|
| WHOLE BODY | | UPPER-HALF BODY | |
| KOI | 4.1 | FAT RATE | 19.2% |
| BODY FAT RATE | 18.60% | FAT MASS | 6.6Kg |
| BODY FAT MASS | 9.4Kg | FAT FREE MASS | 27.7Kg |
| FAT FREE MASS | 40.9Kg | ESTIMATED VOLUME OF MUSCLE | 26.2Kg |
| BMI | 20.6 | | |
| IMPEDANCE | | LOWER-HALF BODY | |
| WHOLE BODY | 577Ω | FAT RATE | 17.5% |
| RIGHT LEG | 258Ω | FAT MASS | 2.8Kg |
| LEFT LEG | 264Ω | FAT FREE MASS | 13.2Kg |
| RIGHT ARM | 293Ω | ESTIMATED VOLUME OF MUSCLE | 12.3Kg |
| LEFT ARM | 290Ω | | |

FIG.16

RIGHT AND LEFT LIMBS BALANCE

RIGHT ARM

| | |
|---|---|
| FAT RATE | 12.4% |
| FAT MASS | 0.4Kg |
| FAT FREE MASS | 2.4Kg |
| ESTIMATED VOLUME OF MUSCLE | 2.3Kg |

LEFT ARM

| | |
|---|---|
| FAT RATE | 12.1% |
| FAT MASS | 0.3Kg |
| FAT FREE MASS | 2.3Kg |
| ESTIMATED VOLUME OF MUSCLE | 2.1Kg |

RIGHT LEG

| | |
|---|---|
| FAT RATE | 17% |
| FAT MASS | 1.4Kg |
| FAT FREE MASS | 6.7Kg |
| ESTIMATED VOLUME OF MUSCLE | 6.2Kg |

LEFT LEG

| | |
|---|---|
| FAT RATE | 17.9% |
| FAT MASS | 1.4Kg |
| FAT FREE MASS | 6.5Kg |
| ESTIMATED VOLUME OF MUSCLE | 6.1Kg |

FIG.18

| RESULT OF JUDGMENT |
|---|
| YOU HAVE PROPER VALUE FOR BODY FAT RATE AND BMI, BUT BECAUSE OF HIGHER KOI THAT LEADS TO BURDEN TO YOUR KNEES, YOU ARE LIKELY TO SUFFER FROM OSTEOARTHRITIS.<br>THE REASON FOR WHICH IS THAT YOU HAVE LESSER VOLUME OF LEG MUSCLE. THEREFORE, YOU NEED TO PAY EFFORT TO INCREASE THE VOLUME OF LEG MUSCLE FOR RELIEVING ANY BURDEN TO THE KNEES. |

JUDGMENT RESULT FOR POSSIBILITY OF OCCURRENCE OF OSTEOARTHRITIS

BASIC DATA

| AGE | SEX | HEIGHT | WEIGHT |
|---|---|---|---|
| 73 | M | 155cm | 50.2Kg |

| WHOLE BODY COMPOSITION DIAGNOSIS | | BALANCE FOR UPPER-HALF AND LOWER-HALF BODIES | |
|---|---|---|---|
| WHOLE BODY | | UPPER-HALF BODY | |
| KOI | 4.1 | FAT RATE | 19.2% |
| BODY FAT RATE | 18.60% | FAT MASS | 6.6Kg |
| BODY FAT MASS | 9.4Kg | FAT FREE MASS | 27.7Kg |
| FAT FREE MASS | 40.9Kg | ESTIMATED VOLUME OF MUSCLE | 26.2Kg |
| BMI | 20.6 | | |
| IMPEDANCE | | LOWER-HALF BODY | |
| WHOLE BODY | 577Ω | FAT RATE | 17.5% |
| RIGHT LEG | 258Ω | FAT MASS | 2.8Kg |
| LEFT LEG | 264Ω | FAT FREE MASS | 13.2Kg |
| RIGHT ARM | 293Ω | ESTIMATED VOLUME OF MUSCLE | 12.3Kg |
| LEFT ARM | 290Ω | | |

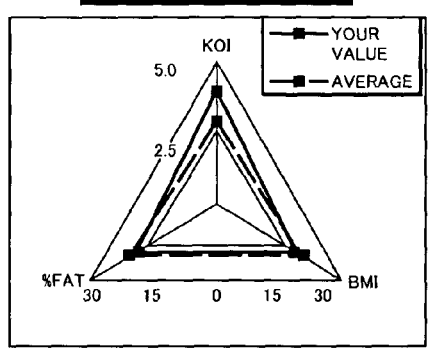

BODY BUILD JUDGMENT VIEW

RIGHT AND LEFT LIMBS BALANCE

| RIGHT ARM | | LEFT ARM | |
|---|---|---|---|
| FAT RATE | 12.4% | FAT RATE | 12.1% |
| FAT MASS | 0.4Kg | FAT MASS | 0.3Kg |
| FAT FREE MASS | 2.4Kg | FAT FREE MASS | 2.3Kg |
| ESTIMATED VOLUME OF MUSCLE | 2.3Kg | ESTIMATED VOLUME OF MUSCLE | 2.1Kg |

| RIGHT LEG | | LEFT LEG | |
|---|---|---|---|
| FAT RATE | 17% | FAT RATE | 17.9% |
| FAT MASS | 1.4Kg | FAT MASS | 1.4Kg |
| FAT FREE MASS | 6.7Kg | FAT FREE MASS | 6.5Kg |
| ESTIMATED VOLUME OF MUSCLE | 6.2Kg | ESTIMATED VOLUME OF MUSCLE | 6.1Kg |

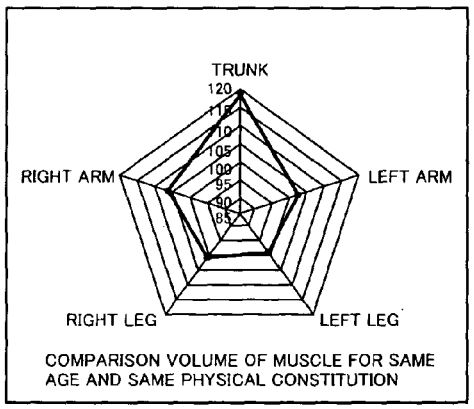

VOLUME OF MUSCLE FOR EACH OF PARTS

COMPARISON VOLUME OF MUSCLE FOR SAME AGE AND SAME PHYSICAL CONSTITUTION

RESULT OF JUDGMENT

YOU HAVE PROPER VALUE FOR BODY FAT RATE AND BMI, BUT BECAUSE OF HIGHER KOI THAT LEADS TO BURDEN TO YOUR KNEES, YOU ARE LIKELY TO SUFFER FROM OSTEOARTHRITIS. THE REASON FOR WHICH IS THAT YOU HAVE LESSER VOLUME OF LEG MUSCLE. THEREFORE, YOU NEED TO PAY EFFORT TO INCREASE THE VOLUME OF LEG MUSCLE FOR RELIEVING ANY BURDEN TO THE KNEES.

… # METHOD AND APPARATUS FOR JUDGMENT OF PHYSICAL CONSTITUTION AND PHYSICAL STRENGTH FOR PERSON UNDER TEST

CROSS-REFERENCE TO RELATED APPLICATION

This application is claiming the benefit of Japanese patent application no. 2002-247808 filed on Aug. 27, 2002 in the name of Tanita Corporation.

BACKGROUND OF THE INVENTION

1. Field of the Invention

The present invention relates to judgment of physical constitution and physical strength for a person under test, and more particularly to, an apparatus and a method for judgment of physical constitution and physical strength for a person under test, which is effective to determine whether the person has good or healthy physical constitution and physical strength that does not tend to suffer from adult non-communicable disease such as adiposity, etc., or that can spend daily life in easy circumstances without any possibility of keeping in bed, by using the data such as body fat rate, BMI (Body Mass Index), "Proportion Age" and "Physical Strength Age" of the person.

2. Description of the Related Art

In the prior art, body fat rate and BMI that is the ratio of body weight to a square of height have been used for an index for judgment of physical constitution of a person.

However, even if a person has the same body fat rate, different result of judgment may be produced depending on whether the person has excessive body weight or is slender in build. In addition, because of BMI determined simply by body weight and height of a person it may happen that some increase in body weight due to muscle is erroneously judged to be adiposity. In the prior art BMI device the judgment of adiposity has been done depending only on the values of body fat and BMI, and therefore, knowledge of a user has been indispensable for the true judgment of adiposity.

Among various effects of adiposity on the body of a person it has been known that any excessive body weight due to adiposity or any reduction in volume of muscle in lower limbs for fixing a knee would impose greater burden to the knee, which may lead to osteoarthritis. In prior art judgment of adiposity performed depending on body fat rate and BMI, however, it has been impractical to judge the possibility of occurrence of osteoarthritis.

In view of the above it is an object of the present invention to provide a new and improved apparatus and method for judgment of physical constitution and physical strength for a person under test, which is effective to systematically evaluate body fat rate, BMI, and distribution of fat and muscle, to graphically display the result of evaluation, and to easily understand the determination as to whether the person has good or healthy physical constitution and physical strength without the need of expert knowledge.

It is another object of the present invention to provide a new and improved apparatus and method for judgment of physical constitution and physical strength for a person under test, which is effective to judge the possibility of occurrence of osteoarthritis and at least one of its causes.

SUMMARY OF THE INVENTION

According to one aspect of the present invention there is provided a method for judgment of physical constitution and physical strength for a person under test, comprising the step of:

calculating Proportion Age based on fat mass in a trunk and fat mass in lower limbs of the person under test.

According to another aspect of the present invention there is provided a method for judgment of physical constitution and physical strength for a person under test, comprising the step of:

calculating Physical Strength Age based on weight of an upper-half body and volume of muscle in lower limbs of the person under test.

According to further aspect of the present invention there is provided a method for judgment of physical constitution and physical strength for a person under test, comprising the step of:

judging the physical constitution and physical strength based on at least one of body fat rate, BMI, Proportion Age and Physical Strength Age of the person under test.

According to one embodiment of the present invention the Proportion Age is calculated based on fat mass in a trunk and fat mass in lower limbs of the person under test.

According to another embodiment of the present invention the Physical Strength Age is calculated based on weight of an upper-half body and volume of muscle in lower limbs of the person under test.

According to yet further aspect of the present invention there is provided a method for judgment of physical constitution and physical strength for a person under test, comprising the step of:

calculating KOI (Knee Osteoarthritis Index) for osteoarthritis based on body weight and volume of muscle in lower limbs of the person under test.

According to one embodiment of the present invention the KOI is corrected based on at least one of shape parameters for a knee of the person under test.

According to another embodiment of the present invention the shape parameter for a knee includes girth of a knee and degree of bow-legs of the person under test.

According to yet further aspect of the present invention there is provided a method for judgment of physical constitution and physical strength for a person under test, comprising the step of:

judging the possibility of occurrence of osteoarthritis and at least one of its causes, based on at least one of BMI and body fat rate as well as KOI for osteoarthritis.

According to one embodiment of the present invention the KOI is calculated based on body weight and volume of muscle in lower limbs of the person under test.

According to another embodiment of the present invention the cause for osteoarthritis includes excessive body weight, less volume of muscle in lower limbs, small girth of a knee, and greater degree of bow-legs of the person under test.

According to yet further aspect of the present invention there is provided an apparatus for judgment of physical constitution and physical strength for a person under test, comprising: a first input unit; a second input unit; and an arithmetic unit; wherein said first input unit enters fat mass in a trunk of the person under test;

said second input unit enters fat mass in lower limbs of the person under test; and said arithmetic unit calculates Proportion Age based on the data entered from said first and second input units.

According to one embodiment of the present invention the first input unit is a body fat meter.

According to another embodiment of the present invention the first input unit is a key unit by which said fat mass in the trunk can manually be entered.

According to further embodiment of the present invention the second input unit is a body fat meter.

According to yet further embodiment of the present invention the second input unit is a key unit by which said fat mass in the lower limbs can manually be entered.

According to yet further aspect of the present invention there is provided an apparatus for judgment of physical constitution and physical strength for a person under test, comprising: a first input unit; a second input unit; and an arithmetic unit; wherein said first input unit enters weight of an upper-half body of the person under test;

said second input unit enters volume of muscle in lower limbs of the person under test; and said arithmetic unit calculates Physical Strength Age based on the data entered from said first and second input units.

According to one embodiment of the present invention the first input unit is a weight meter.

According to another embodiment of the present invention the first input unit is a key unit by which said weight of the upper-half body can manually be entered.

According to further embodiment of the present invention the second input unit is a body fat meter.

According to yet further embodiment of the present invention the second input unit is a key unit by which said volume of muscle in lower limbs can manually be entered.

According to yet further aspect of the present invention there is provided an apparatus for judgment of physical constitution and physical strength for a person under test, comprising: a first input unit; a second input unit; a third input unit; a fourth input unit; a judgment unit; and a display unit, wherein said first input unit enters body fat rate of the person under test;

said second input unit enters BMI (Body Mass Index) of the person under test;

said third input unit enters Proportion Age of the person under test;

said fourth input unit enters Physical Strength Age of the person under test;

said judgment unit judges the physical constitution and physical strength based on the data from at least one of the first, second, third and fourth input units; and said display unit displays the result of judgment performed by the judgment unit.

According to one embodiment of the present invention the display unit graphically displays the result of judgment.

According to another embodiment of the present invention the first input unit is a body fat meter.

According to further embodiment of the present invention the first input unit is a key unit by which said body fat rate can manually be entered.

According to yet further embodiment of the present invention the second input unit is a key unit by which said BMI can manually be entered.

According to yet further embodiment of the present invention the third input unit calculates the Proportion Age based on fat mass in the trunk and fat mass in the lower limbs of the person under test.

According to yet further embodiment of the present invention the third input unit is a key unit by which the Proportion Age can manually be entered.

According to yet further embodiment of the present invention the fourth input unit calculates the Physical Strength Age based on weight of the upper-half body and volume of muscle in the lower limbs of the person under test.

According to yet further embodiment of the present invention the fourth input unit is a key unit by which the Physical Strength Age can manually be entered.

According to yet further aspect of the present invention there is provided an apparatus for judgment of physical constitution and physical strength for a person under test, comprising: a first input unit; a second input unit; and an arithmetic unit, wherein said first input unit enters body weight of the person under test;

said second input unit enters volume of muscle in lower limbs of the person under test; and said arithmetic unit calculates KOI (Knee Osteoarthritis Index) for osteoarthritis based on the data from the first and second input units.

According to one embodiment of the present invention the first input unit is a weight meter.

According to another embodiment of the present invention the first input unit is a key unit by which said body weight can manually be entered.

According to further embodiment of the present invention the second input unit is a body fat meter.

According to yet further embodiment of the present invention the second input unit is a key unit by which said volume of muscle in the lower limbs can manually be entered.

According to yet further embodiment of the present invention the KOI is corrected according to at least one of shape parameters for a knee of the person under test.

According to yet further embodiment of the present invention the shape parameter for a knee includes girth of a knee and degree of bow-legs of the person under test.

According to yet further aspect of the present invention there is provided an apparatus for judgment of physical constitution and physical strength for a person under test, comprising: a first input unit; a second input unit; a third input unit; a judgment unit; and a display unit, wherein said first input unit enters BMI (Body Mass Index) of the person under test;

said second input unit enters body fat rate of the person under test;

said third input unit enters KOI (Knee Osteoarthritis Index) for osteoarthritis of the person under test;

said judgment unit judges the possibility of occurrence of osteoarthritis and at least one of its causes, based on the data from at least one of said first and second input units as well as the data from said third input unit; and said display unit displays the result of judgment performed by said judgment unit.

According to one embodiment of the present invention the first input unit is a key unit by which said BMI can manually be entered.

According to another embodiment of the present invention the second input unit is a body fat meter.

According to further embodiment of the present invention the second input unit is a key unit by which said body fat rate can manually be entered.

According to yet further embodiment of the present invention the third input unit calculates said KOI based on body weight and volume of muscle in lower limbs of the person under test.

According to yet further embodiment of the present invention the third input unit is a key unit by which said KOI can manually be entered.

According to yet further embodiment of the present invention the KOI is corrected according to at least one of shape parameters for a knee of the person under test.

According to yet further embodiment of the present invention the shape parameter for a knee includes girth of a knee and degree of bow-legs of the person under test.

According to yet further embodiment of the present invention the cause for osteoarthritis includes excessive body weight, less volume of muscle in lower limbs, small girth of a knee, and greater degree of bow-legs of the person under test.

BRIEF DESCRIPTION OF THE DRAWINGS

Now, the present invention will be described in more detail with reference to the accompanying drawings, in which:

FIG. 3 is a flow chart illustrating an operation of the judgment apparatus;

FIGS. 4A to 4F are display screens of a display unit;

FIGS. 5A and 5B are display screens of the display unit;

FIG. 9 is a display screen of the display unit;

FIG. 10 is a display screen of the display unit;

FIG. 11 is a display screen of the display unit;

FIG. 14 is a display screen of the display unit;

FIG. 16 is a display screen of the display unit;

FIG. 18 is a display screen of the display unit; and

FIG. 19 is printed sheet of judgment result for the possibility of occurrence of osteoarthritis.

DETAILED DESCRIPTION OF THE PREFERRED EMBODIMENTS

Figure 1:
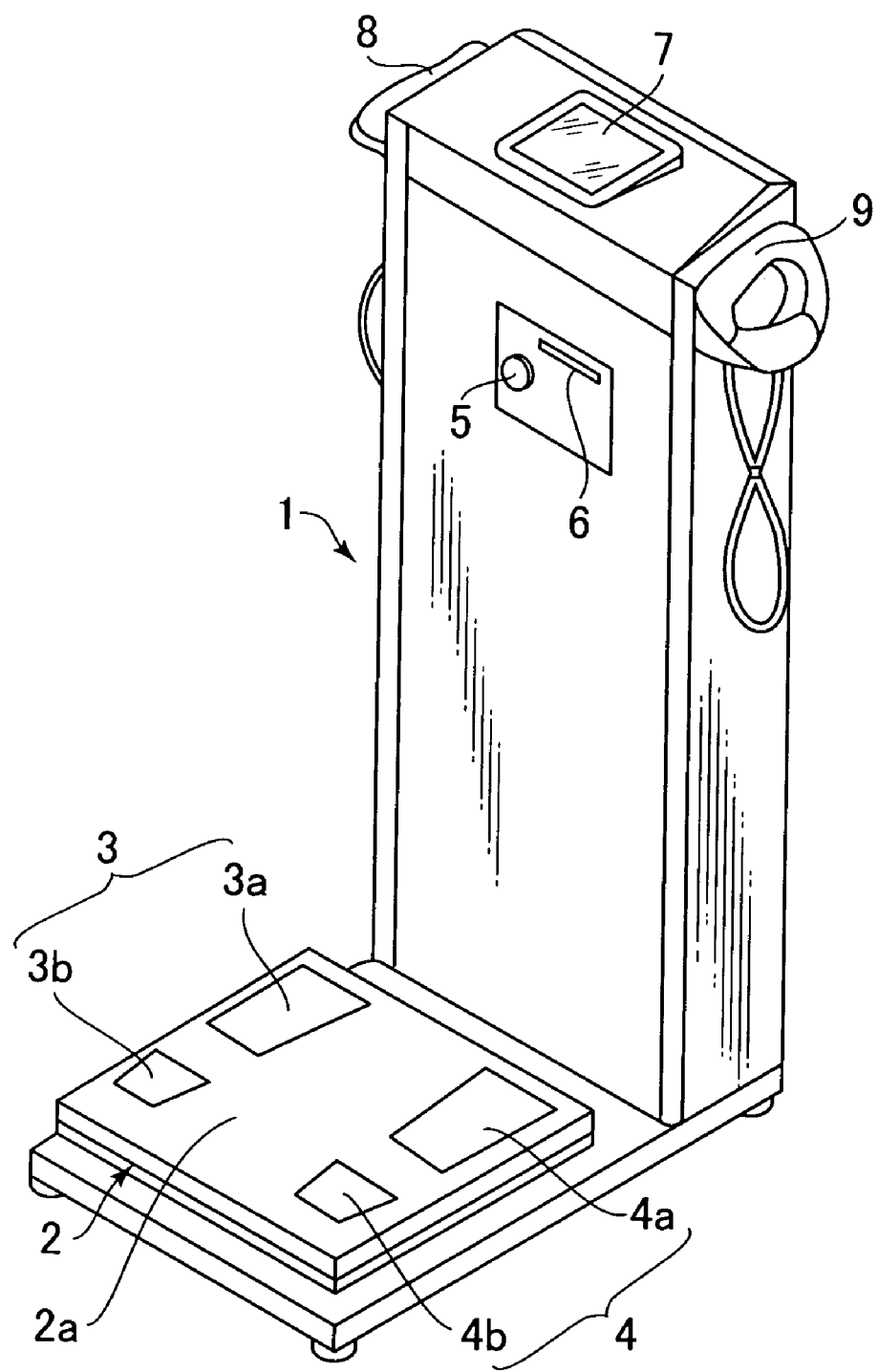
FIG. 1 is a perspective view of an apparatus for judgment of physical constitution and physical strength for a person under test, constructed in accordance with one embodiment of the present invention.

FIG. 1 is a perspective view of an apparatus for judgment of physical constitution and physical strength for a person under test, constructed in accordance with a first embodiment of the present invention. The judgment apparatus 1 is generally shaped as a letter "L" and is provided with a weight meter 2 at the lower portion thereof. The weight meter 2 is of previous type and includes a platform 2a on which a person under test mounts to measure his or her body weight by making contact the right and left soles of the person with electrodes 3, 4 provided on the platform. The electrodes 3, 4 consist of current-supplying electrodes 3a, 4a and voltage-measurement electrodes 3b, 4b. The judgment apparatus 1 further includes a power switch 5 and a printer 6 at the front side thereof. In addition, a display and input unit 7 made by a touch panel type liquid crystal device is provided on the top of the judgment apparatus 1, and left and right hand electrodes 8, 9 are provided on the upper left and right sidewalls of the judgment apparatus 1. The hand electrodes 8, 9 consist of current-supplying electrodes 8a, 9a and voltage-measurement electrodes 8b, 9b. Further description of the hand electrodes are omitted, here, because it is well known in the art of "hand type body fat meter".

Figure 2:
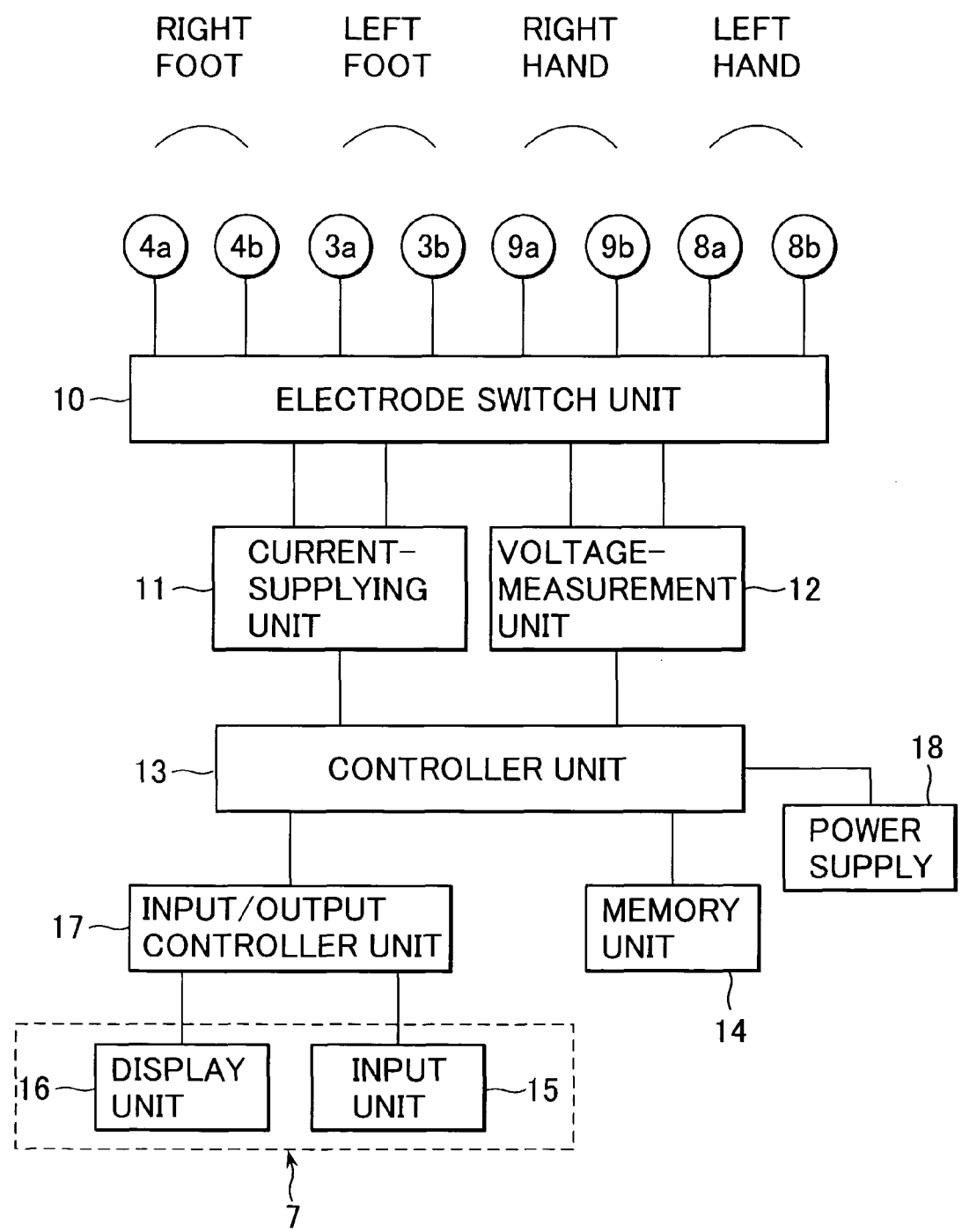
FIG. 2 is an electric block diagram of the judgment apparatus in FIG. 1.

FIG. 2 is an electric block diagram of the judgment apparatus 1. The eight electrodes adapted to make contact with the left and right feet and hands of the person under test 3a, 3b, 4a, 4b, 8a, 8b, 9a, 9b are connected to an electrode switch unit 10. The electrode switch unit 10 is connected to a controller unit 13 via a current-supplying unit 11 and a voltage-measurement unit 12. The controller unit 13 includes a microcomputer and is connected to a memory unit 14 for storing various types of data. The display and input unit 7, as illustrated in FIG. 1, is divided into an input unit 15 and a display unit 16 in view of electrical circuitry, both of which are connected to the controller unit 13 via an input/output controller unit 17. Reference number 18 represents a power supply for supplying electric power to the controller unit 13 and other units.

FIG. 3 is a flow chart illustrating an operation of the judgment apparatus 1. Initially, when the power switch 5 of the judgment apparatus 1 is turned ON, all the electrical units within the apparatus are initialized at Step S1, and the routine proceeds to tare weight input mode as shown in FIG. 4A at step S2. In this mode, some message for prompting the person under test to enter the tare weight and a keyboard for entering the tare weight are displayed on the display unit 16. After the tare weight of, for example, 1.5 kg of the person under test is entered by number keys of the keyboard on the display unit with his or her fingers, the screen as shown in FIG. 4B is displayed. After a "Proceed" key is depressed then the routine proceeds to step S3. In this respect, if wrong value of tare weight has been entered, then all the entered digits may be erased at a time by a "Erase" key or the entered digits may be erased one by one by a "Back" key and the correct numbers may be re-entered.

At step S3, measurement of body weight of the person under test is performed. In particular, as shown in FIG. 4C, the person under test is prompted to mount on the platform 2a of the weight meter 2 with bare feet, and the value of tare weight entered at step S2 is displayed with a "minus (−)" sign added in order to mean subtraction of the tare weight. When the person under test mounts on the platform 2a of the weight meter 2, it measures the body weight of the person under test and, as shown in FIG. 4D, the value of the body weight is displayed together with some message for prompting the person to proceed to the next step. If the "Proceed" key is depressed the routine proceeds to step S4 wherein, as shown in FIG. 4E, the physical constitution and sex of the person under test are set. For example, a "Standard/Man" key is depressed. Then, the "Proceed" key is depressed to proceed to step S5. At this step S5, as shown in FIG. 4F, the number keys of the keyboard are used to enter the age of the person under test and the "Proceed" key is depressed to proceed to step S6. At this step S6, as shown in FIG. 5A, the number keys of the keyboard are used to enter the height of the person under test. Then, the "Proceed" key is depressed to proceed to step S7 wherein the data of the person under test measured and entered at steps S3 to S6 is displayed on the display unit 16, as shown in FIG. 5B. If a "Return" key or a "Stop" key is depressed, here, the routine returns to step S2 from which the input and measurement operations as described above are performed once again. However, if a "Start" key is depressed, here, the routine proceeds to step S9 to start measurement of each of the parts of the person under test.

At step S9 the switch unit 10 is switched in response to a command from the controller unit 13 so that the current-supplying unit 11 supplies AC current to the electrodes 3a, 4a and the voltage-measurement unit 12 measures the voltage between the electrodes 3b and 4b. Based on those supplied current and measured voltage the controller unit 13 calculates bioelectrical impedance (BI) between both feet of the person under test. In the same manner the BI for each of the parts: a whole body, a right foot, a left foot, a right hand and a left hand of the person under test is measured. At step S10 the measured values of BI are stored in the memory unit 14.

At step S11 the body fat rate, fat free mass and body fat mass of the person under test is calculated based on the measured values of BI. More particularly, at first, the body fat rate, fat free mass and body fat mass in a whole body of the person under test is calculated based on the body weight and the BI for the whole body. Then, the body fat rate, fat free mass and body fat mass in each of the parts: right foot, left foot, right hand and left hand of the person under test is calculated based on the BI for each of such parts. Next, sum of the body fat mass in each of the parts is subtracted from the body fat mass in the whole body to produce the body fat mass in the trunk. In the same manner, sum of the fat free mass for each of the parts is subtracted from the fat free mass for the whole body to produce the fat free mass for the trunk. Thereafter, the body fat mass in the trunk is added to the fat free mass for the trunk to produce the weight for the trunk.

At step S12 an estimated volume of muscle is determined. More particularly, because of knowledge of correlation between the fat free mass and the volume of bone, estimation of the volume of bone is performed based on the fat free mass and the volume of bone is subtracted from the fat free mass to derive the estimated volume of muscle.

Figure 6:
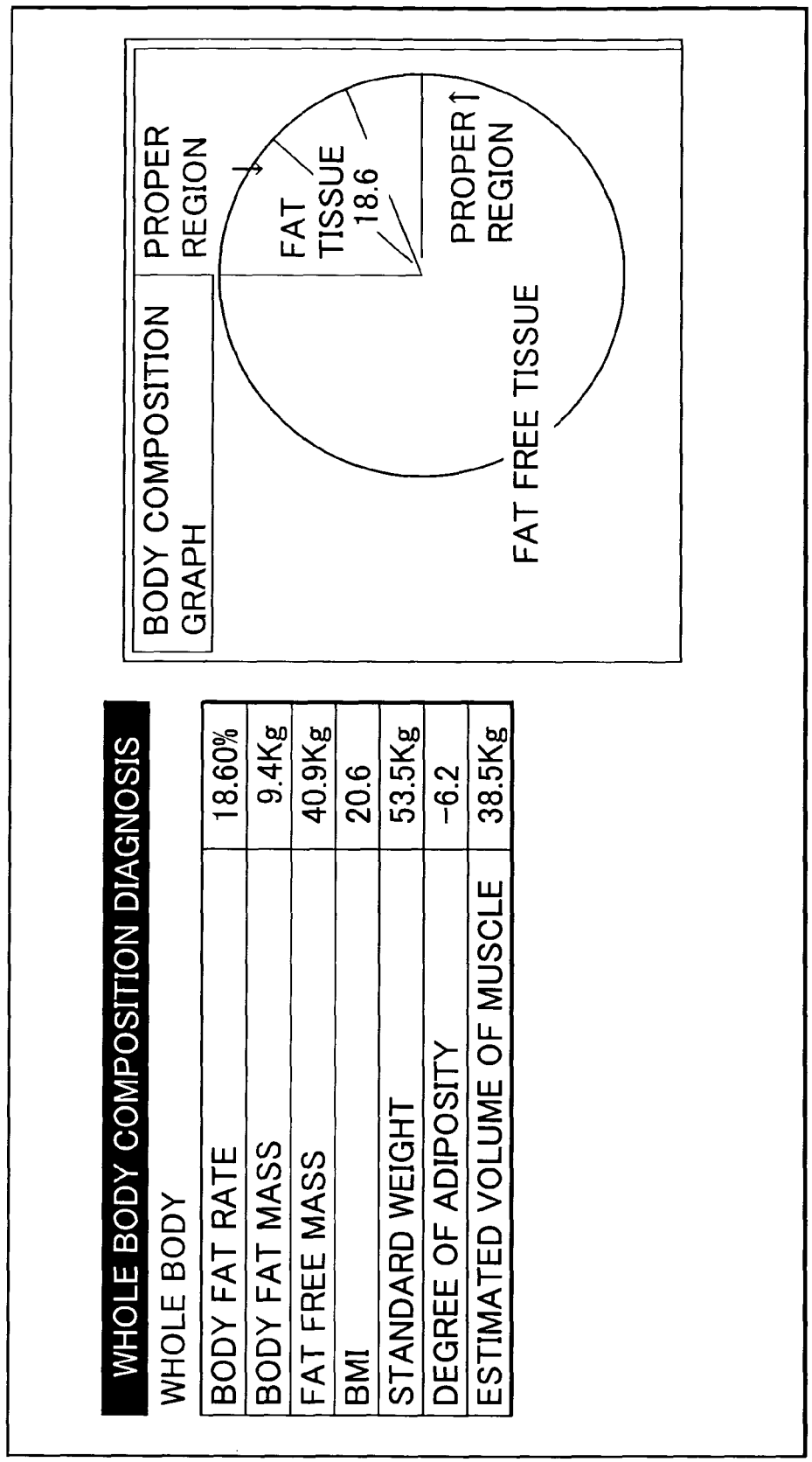
FIG. 6 is a display screen of the display unit.

At step S13 the BMI, standard weight and degree of adiposity of the person under test are calculated based on the body weight and the height. Then, the body fat rate, body fat mass, fat free mass, BMI, standard weight and degree of adiposity for the whole body is displayed in tabular form on the display unit 16 at the left side area thereof, as shown in FIG. 6. In this connection it is noted that the standard weight is defined as such weight that is resulted when BMI is 22. The degree of adiposity is defined by the following formula:

Degree of adiposity (%){(measured weight–standard weight)/standard weight}×100

In addition, the body fat rate is displayed in the form of circle graph on the display unit at the right side area thereof, as shown in FIG. 6. The graph represents the proper region for body fat rate, which facilitates judgment as to whether the body fat for the person under test is greater or lesser.

Figure 7A:
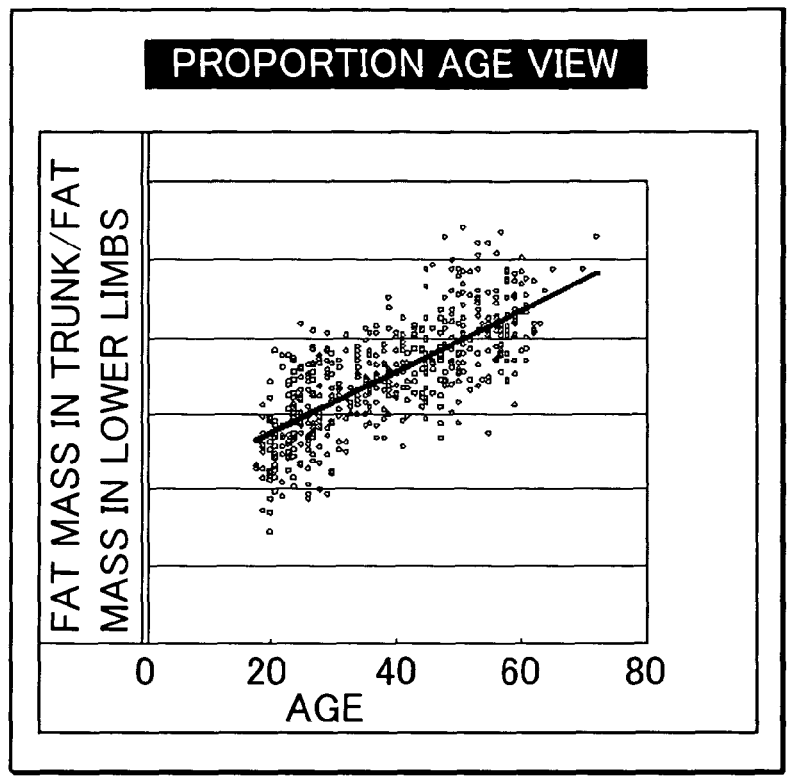
FIGS. 7A and 7B each is a view of Proportion Age.
Figure 7B:
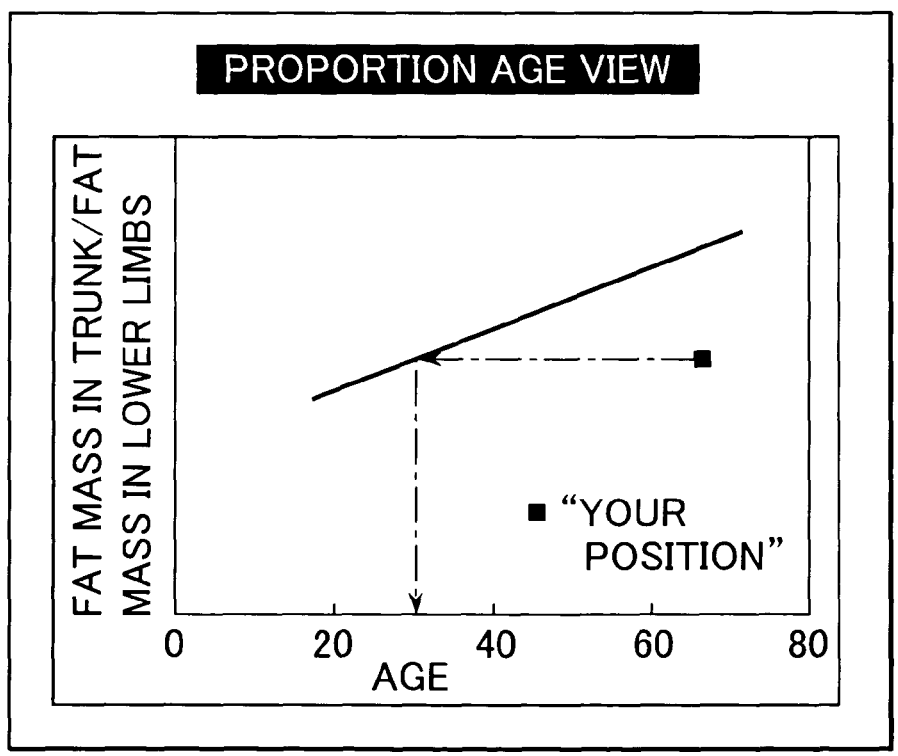

At step S14 "Proportion Age" of the person under test is calculated. FIG. 7A is a graph plotting "fat mass in trunk/fat mass in lower limbs" on the ordinate and the age on the abscissa. This graph shows distribution of the fat from which it is apparent that there is some correlation between the fat mass in trunk/fat mass in lower limbs and the age. Accordingly, if a regression curve that is indicated by a solid line in the graph is derived, the age of the person under test can be determined from the data of fat mass in trunk/fat mass in lower limbs. Such age is, here, referred to as "Proportion Age". At step S14 the screen as shown in FIG. 7B is ultimately displayed on the display unit 16 wherein "Your Position" indicates "Proportion Age" of the person under test. More particularly, in this example, the age on the abscissa corresponding to a point on the regression curve at the level of the ordinate (the value of fat mass in the trunk/fat mass in the lower limbs) that correspond to "Your Position" is "Proportion Age" that equals twenty-five (25) years old. In this respect it is noted that the fat mass in upper-half body, the total fat mass, the body weight, or the fat mass in an arm may be used, instead of the fat mass in trunk. Furthermore, the fat mass in both feet, or the fat mass in a single foot, or even the total fat mass may be used for the fat mass in lower limbs. In addition, a reciprocal of the fat mass in trunk/fat mass in lower limbs, i.e. the fat mass in lower limbs/fat mass in trunk may be used. An experiment shows that with the progress of aging an increase in fat mass in the upper-half body becomes greater than that for the lower-half body. In particular, an increase in fat mass in trunk is significant, and therefore, the fat mass in the trunk/fat mass in the lower limbs is selected to plot on the ordinate in the most preferred embodiment.

Figure 8A:
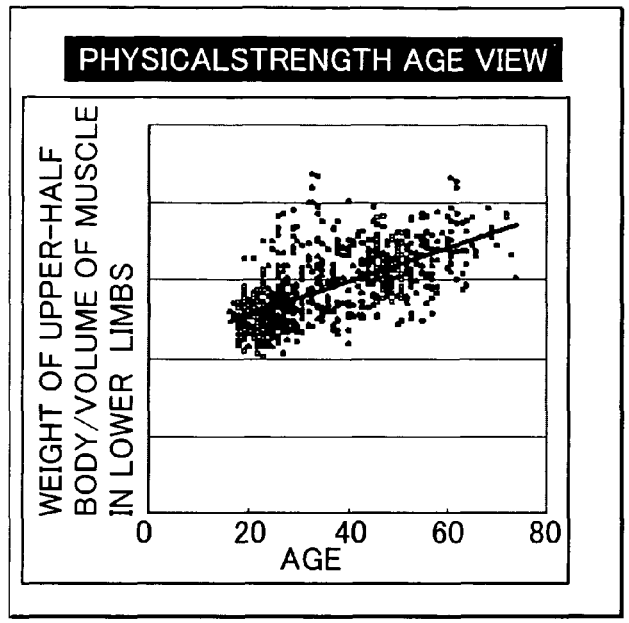
FIGS. 8A and 8B each is a view of Physical Strength Age.
Figure 8B:
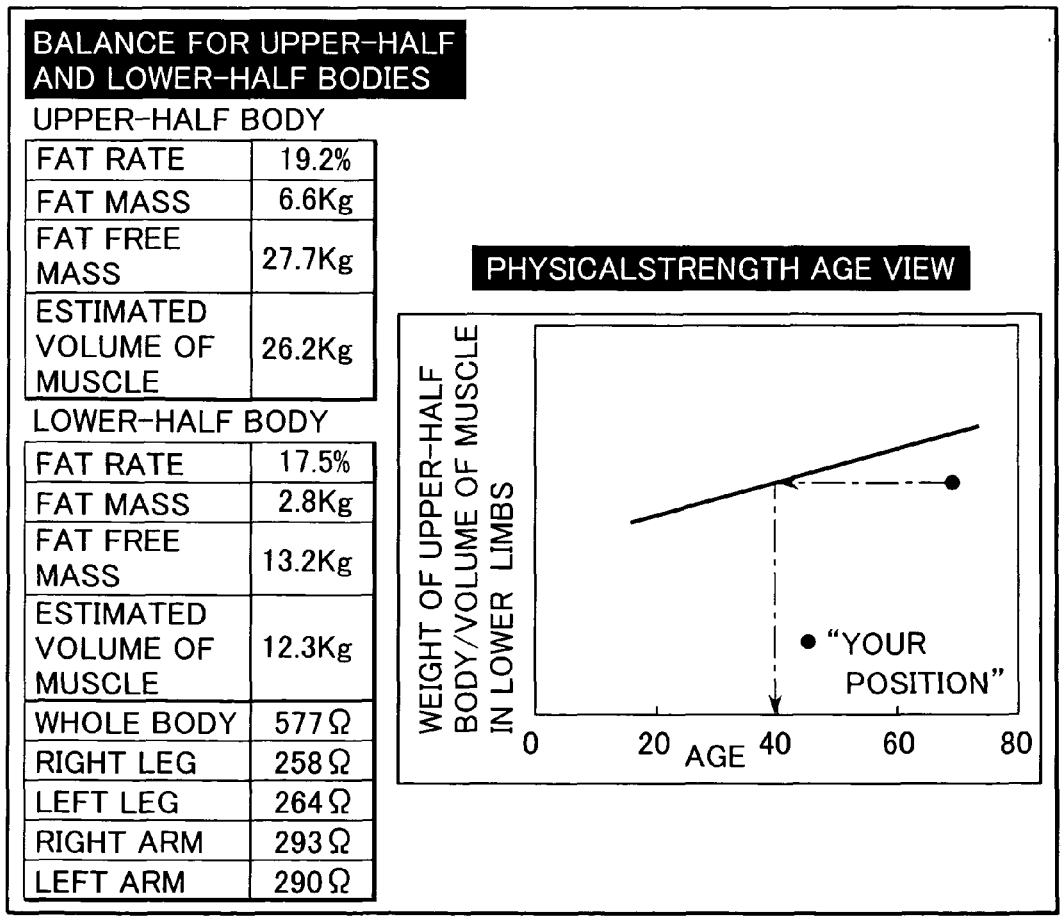

At step S15 "Physical Strength Age" of the person under test is calculated. FIG. 8A is a graph plotting "weight of upper-half body/volume of muscle in lower limbs" on the ordinate and the age on the abscissa. The weight of upper-half body/volume of muscle in lower limbs represents how much burden is imposed to the muscle in lower limbs when walking, or weight of upper-half body supported by unit volume of muscle in lower limbs, and hence, an activity of the person under test. It is apparent in the graph that there is some correlation between the weight of upper-half body/volume of muscle in lower limbs and the age. Accordingly, if a regression curve that is indicated by a solid line in the graph is derived, the age of the person under test can be determined from the data of weight of upper-half body/volume of muscle in lower limbs. Such age is, here, referred to as "Physical Strength Age". At step S15 the screen as shown in FIG. 8B is ultimately displayed on the display unit 16 wherein "Your Position" indicates "Physical Strength Age" of the person under test. More particularly, in this example, the age on the abscissa corresponding to a point on the regression curve at the level of the ordinate (the weight of upper-half body/volume of muscle in lower limbs) that correspond to "Your Position" is "Physical Strength Age" that equals forty (40) years old. The display unit 16 displays, on the left side area thereof, the fat rate, fat mass, fat free mass and estimated volume of muscle for each of upper-half body and lower-half body in tabular form, which are the concrete values for "Your Position". Accordingly, the degree of how much the upper and lower-half bodies are unbalanced from each other can be known.

In this step the fat free mass may be used, instead of the volume of muscle. Furthermore, the body weight, the volume of muscle in upper-half body, the volume of muscle in trunk, or the volume of muscle in an arm may be used, instead of the weight of upper-half body. The volume of muscle in both feet or in a single foot may be used for the volume of muscle in lower limbs.

At step S16 a radar chart prepared based on the body fat rate, BMI, Proportion Age and Physical Strength Age is displayed on the display unit 16, as shown in FIG. 9. Because of standard values shown on the chart it is possible to easily determine whether the physical constitution and physical strength for a person under test is good or not. For the purpose of illustration of the present invention the term "physical constitution" refers to an external body condition of a person such as height, body weight, skeletal structure, nutritive condition, etc. In particular, "good physical constitution" means such condition of a person that does not tend to suffer from adult non-communicable disease such as adiposity, etc. On the other hand, the term "physical strength" refers to a physical ability to work and exercise or to make resistance against diseases. In particular, "good physical strength" means at least such condition of a person that can spend daily life in easy circumstances without any possibility of keeping in bed.

At step S17 the display unit 16 displays a proportion judgment view, as shown in FIG. 10. The proportion judgment view shows the body fat rate, body fat mass, fat free mass and estimated volume of muscle for each of the parts: trunk, both hands and both feet of the person under test. Accordingly, the person under test can objectively judge his or her body characteristic at a glance.

At step S18 the display unit 16 displays the final judgment result synthetically derived from the results for steps S13 to S17, as shown in FIG. 11.

Figure 12:
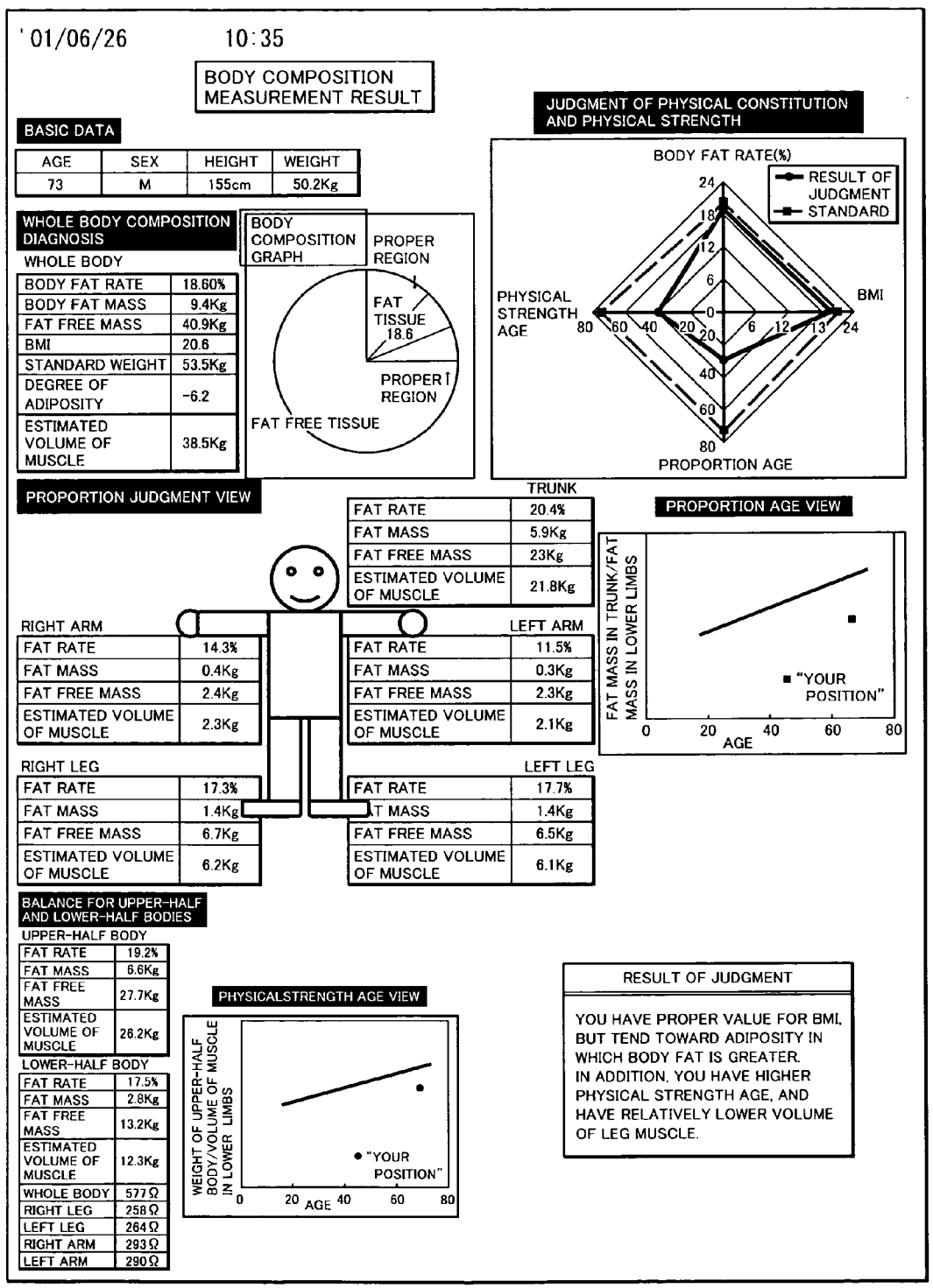
FIG. 12 is a printed sheet of body composite measurement result.

At step S19 a body composition measurement result in which all the results displayed are collected into one sheet, as shown in FIG. 12, is printed by the printer device 6.

The judgment apparatus in the first embodiment has been described as having capability to automatically calculate the body fat rate, BMI, Proportion Age and Physical Strength Age. However, it may, of course, be possible that measurement with the conventional body fat meter, manual calculation, etc., are used to produce the body fat rate, BMI, Proportion Age and Physical Strength Age for judgment of physical constitution and physical strength.

Now, an apparatus for judgment of physical constitution and physical strength for a person under test, constructed in accordance with a second embodiment of the present invention in which the possibility of occurrence of osteoarthritis and its causes are determined will be described. The perspective view and electrical block diagram of the apparatus in the first embodiment are again applied to the apparatus in the second embodiment.

Figure 13:
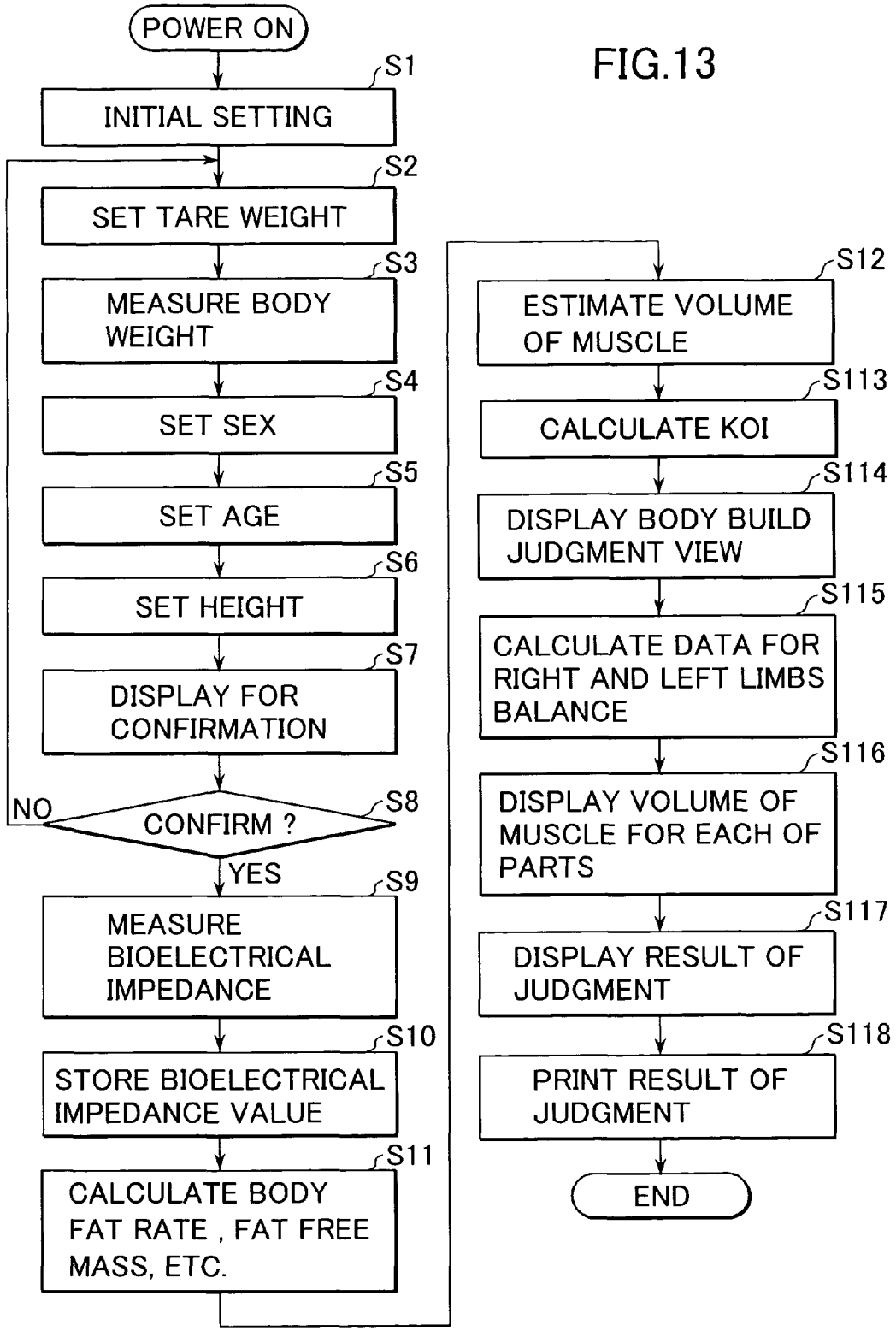
FIG. 13 is a flow chart illustrating an operation of a judgment apparatus according to a second embodiment of the present invention.

Referring to a flow chart of FIG. 13, an operation of the judgment apparatus in the second embodiment will be described. The steps in FIG. 13 that operate in the same manner as those in FIG. 3 are referenced by the same reference characters. Description of steps S1 to S12 in FIG. 13 is omitted because they operate in the same manner as those in FIG. 3.

At step S113 the BMI is calculated based on the body weight and height of the person under test. In addition, "KOI" (Knee Osteoarthritis Index) for osteoarthritis is calculated, and the KOI, body fat rate, fat mass, fat free mass and BMI for whole body are displayed in tabular form on the display unit 16, as shown in left side area of FIG. 14. The KOI is defined by the following formula:

KOI=body weight/volume of muscle in lower limbs

This formula calculates KOI based on the body weight and the volume of muscle in lower limbs, but precision of KOI can be enhanced if any correction is made with knee shape parameters such as girth of a knee, degree of bow-legs (which is defined as the separation between both knees when a person stands and closes his or her legs), etc.

Then, the fat rate, fat mass, fat free mass and estimated volume of muscle for each of upper-half and lower-half bodies are displayed in tabular form on the display unit 16, as shown in FIG. 14.

Figure 15:
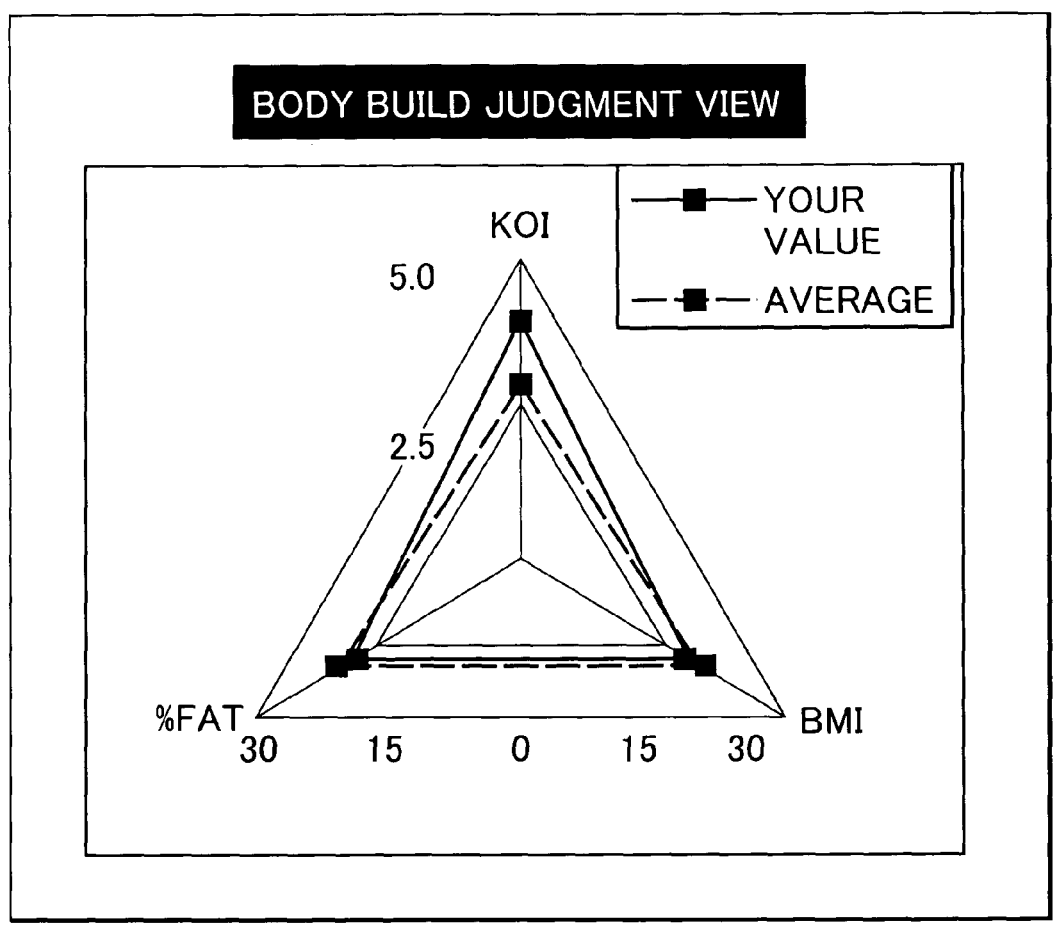
FIG. 15 is a display screen of the display unit.

At step S114 a radar chart illustrating KOI, BMI, and % FAT (body fat rate) is displayed on the display unit 16, as shown in FIG. 15. Because of average values shown on the chart by a broken line it is possible to easily determine the possibility of occurrence of osteoarthritis and its causes using the radar chart or body build judgment view. In particular, in this example, KOI is higher than the average value, which means that the possibility of occurrence of osteoarthritis is higher. In addition, the physical constitution represented by the body fat rate and BMI is substantially at the average level, and therefore, no osteoarthritis can be caused due to the body weight, but it is the problem that the volume of muscle in lower limbs is lesser.

At step S115 the fat rate, fat mass, fat free mass and estimated volume of muscle for each of the parts: right arm, left arm, right leg and left leg are displayed in tabular form on the display unit 16, as shown in FIG. 16.

Figure 17:
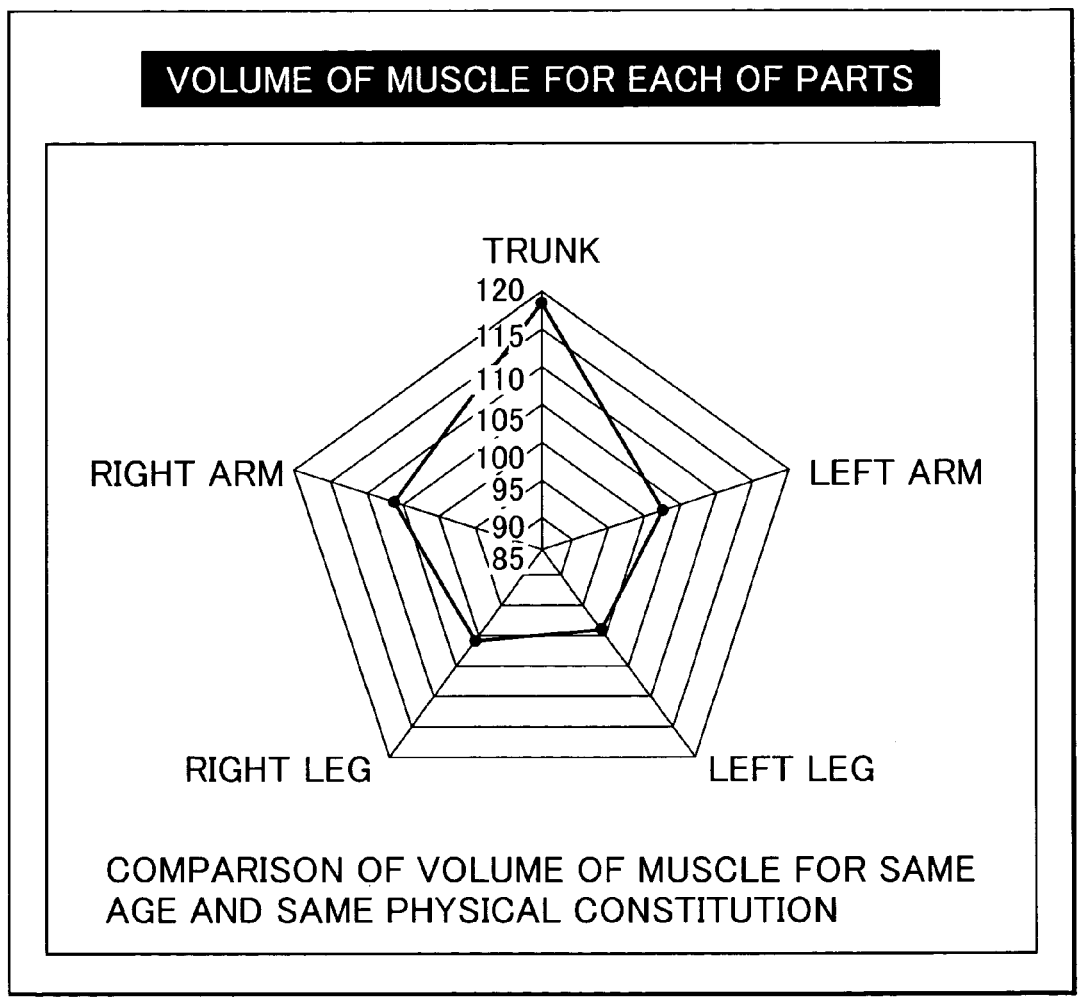
FIG. 17 is a display screen of the display unit.

At step S116 a radar chart illustrating the volume of muscle in each of the parts: trunk, left arm, left leg, right leg and right arm is displayed on the display unit 6, as shown in FIG. 17. It is assumed, here, that the volume of muscle for the same age and the same BMI is set at 100. Accordingly, the person under test can objectively judge his or her own volume of muscle at a glance.

At step S117 a final judgment result provided from the respective results for steps S113 to S116 is displayed on the display unit 16 as a message, as shown in FIG. 18. The message includes at least (1) the possibility of occurrence of osteoarthritis and (2) at least one of its causes. The cause for osteoarthritis includes excessive body weight, less volume of muscle in lower limbs, small girth of a knee, and greater degree of bow-legs of the person under test. In an example in FIG. 18 the cause includes (1) higher KOI or higher possibility of occurrence of osteoarthritis, and (2) lesser volume of muscle in legs. Furthermore, the judgment may be done on the basis of the age and the shape of a knee of the person under test.

At step S118 a judgment result for possibility of occurrence of osteoarthritis in which all the results displayed are collected into one sheet, as shown in FIG. 19, is printed by the printer device 6.

The currently preferred embodiments of an apparatus and method for judgment of physical constitution and physical strength for a person under test have been described above. However, the present invention is not limited to such embodiments, but various modification and correction may be done within the scope of the present invention as defined in the claims.

The present invention provides an advantage in that because of "Proportion Age" calculated based on fat mass in a trunk and fat mass in lower limbs of a person under test it is possible for the person under test to clearly understand how far the value of his or her Proportion Age is apart from its standard value.

The present invention provides an additional advantage in that because of "Physical Strength Age" calculated based on weight of upper-half body and volume of muscle in lower limbs of the person under test it is possible to directly determine whether the person under test has such degree of physical strength that can spend daily life in easy circumstances.

In addition, because of judgment of physical constitution and physical strength performed based on body fat rate, BMI, Proportion Age and Physical Strength Age of the person under test it is possible not only to determine whether the person under test has good physical constitution and physical strength that does not tend to suffer from adiposity, but also to determine whether the person under test has such physical strength that can spend daily life in easy circumstances without any possibility of keeping in bed.

Furthermore, because of KOI (Knee Osteoarthritis Index) for osteoarthritis calculated based on body weight and volume of muscle in lower limbs of the person under test it becomes easy to judge the possibility of occurrence of osteoarthritis according to KOI. Moreover, because of judgment of the possibility of occurrence of osteoarthritis and its cause performed based on at least one of BMI and body fat rate as well as KOI for osteoarthritis it is possible for any person under test to easily know how much burden is imposed to his or her knee(s) and why such burden is imposed, and hence, to easily get nearer the ideal body build that has lower possibility of occurrence of osteoarthritis.

What is claimed is:

1. An apparatus for judgment of physical constitution and physical strength for a person under test, comprising:
    a first input unit;
    a second input unit;
    a third input unit;
    a fourth input unit;
    a judgment unit; and
    a display unit,
    wherein said first input unit enters body fat rate of the person under test;
    said second input unit enters BMI (Body Mass Index) of the person under test;
    said third input unit enters Proportion Age of the person under test, the Proportion Age being determined from the correlation between age and the ratio fat mass in the trunk/fat mass in the lower limbs;
    said fourth input unit enters Physical Strength Age of the person under test, the Physical Strength Age being determined by the correlation between age and the ratio weight of upper-half body/volume of muscle in lower limbs;
    said judgment unit judges the physical constitution and physical strength based on the data from at least one of the first, second, third and fourth input units using the data from at least one of the third and fourth input units; and
    said display unit displays the result of judgment performed by the judgment unit.

2. An apparatus for judgment of physical constitution and physical strength for a person under test according to claim 1 in which said first input unit is a body fat meter.

3. An apparatus for judgment of physical constitution and physical strength for a person under test according to claim 1 or 2 in which said first input unit is a key unit by which said body fat rate can manually be entered.

4. An apparatus for judgment of physical constitution and physical strength for a person under test according to any one of claim 1 in which said second input unit is a key unit by which said BMI can manually be entered.

5. An apparatus for judgment of physical constitution and physical strength for a person under test according to any one of claim 1 in which said third input unit is a key unit by which said Proportion Age can manually be entered.

6. An apparatus for judgment of physical constitution and physical strength for a person under test according to any one of claim 1 in which said fourth input unit is a key unit by which said Physical Strength Age can manually be entered.

* * * * *

UNITED STATES PATENT AND TRADEMARK OFFICE
CERTIFICATE OF CORRECTION

PATENT NO. : 7,125,386 B2 Page 1 of 1
APPLICATION NO. : 10/645752
DATED : October 24, 2006
INVENTOR(S) : Yasuhiro Kasahara It is certified that error appears in the above-identified patent and that said Letters Patent is hereby corrected as shown below:

Column 7 line 51, delete "(%){(measured" and insert instead --(%)={(measured--

Signed and Sealed this

Twenty-fourth Day of February, 2009

JOHN DOLL
*Acting Director of the United States Patent and Trademark Office*